(12) United States Patent
Cumming

(10) Patent No.: US 9,655,717 B2
(45) Date of Patent: *May 23, 2017

(54) SEMI-FLEXIBLE POSTERIORLY VAULTED ACRYLIC INTRAOCULAR LENS FOR THE TREATMENT OF PRESBYOPIA

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/139,637

(22) Filed: Apr. 27, 2016

(65) Prior Publication Data

US 2016/0235520 A1 Aug. 18, 2016

Related U.S. Application Data

(63) Continuation of application No. 14/257,933, filed on Apr. 21, 2014, now Pat. No. 9,351,825, which is a continuation of application No. 14/143,612, filed on Dec. 30, 2013, now abandoned.

(51) Int. Cl.
*A61F 2/16* (2006.01)

(52) U.S. Cl.
CPC .............. *A61F 2/16* (2013.01); *A61F 2/1613* (2013.01); *A61F 2002/169* (2015.04); *A61F 2002/1689* (2013.01); *A61F 2002/16905* (2015.04); *A61F 2230/0006* (2013.01)

(58) Field of Classification Search
CPC .... A61F 2/1629; A61F 2/1613; A61F 2/1648; A61F 2002/1689; A61F 2002/1681
USPC ....................................................... 623/6.21
See application file for complete search history.

(56) References Cited

U.S. PATENT DOCUMENTS

| 2,834,023 | A | 5/1958 | Wolfgang |
| 4,073,014 | A | 2/1978 | Poler |
| 4,118,808 | A | 10/1978 | Poler |
| 4,122,556 | A | 10/1978 | Poler |

(Continued)

FOREIGN PATENT DOCUMENTS

| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — David H Willse
*Assistant Examiner* — Tiffany Shipmon
(74) *Attorney, Agent, or Firm* — Sheppard, Mullin Richter & Hampton LLP

(57) ABSTRACT

An intraocular lens having an optic and at least one semi-rigid, haptic connected to the optic, both of which may be acrylic. The intraocular lens can have a fixed longitudinal length, e.g., the same fixed length pre-operatively and post-operatively. The intraocular lens can resist deformation, despite contraction and relaxation of the ciliary muscle and fibrosis within the capsular bag, after implantation into the eye using, for example, by the semi-rigid haptics. The intraocular lens can be sufficiently flexible to be compressed from an original configuration to a compressed configuration for insertion into the eye through a small incision and return to the original configuration after implantation into the eye.

28 Claims, 2 Drawing Sheets

(56) References Cited

U.S. PATENT DOCUMENTS

| | | |
|---|---|---|
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Parekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |

(56) References Cited

U.S. PATENT DOCUMENTS

| | | |
|---|---|---|
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,932,839 B1 | 8/2005 | Kamerling et al. |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 9,211,186 B2 | 12/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0215340 A1 | 10/2004 | Messner et al. |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2011/0313519 A1 | 12/2011 | Cumming |
| 2011/0313524 A1 | 12/2011 | Cumming |
| 2011/0313525 A1 | 12/2011 | Cumming |
| 2012/0296424 A1 | 11/2012 | Betser |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0245904 A1 | 9/2015 | Cumming |
| 2015/0245905 A1 | 9/2015 | Cumming |
| 2015/0272726 A1 | 10/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |

(56) References Cited

FOREIGN PATENT DOCUMENTS

| WO | WO 2009/086511 | 7/2009 |
| WO | WO 2011/151839 | 12/2011 |

OTHER PUBLICATIONS

International Search Report and Written Opinion for PCT/US13/61452 dated Feb. 24, 2014 in 11 pages.
International Search Report and Written Opinion for PCT/US2014/057037 dated Jan. 20, 2015 in 12 pages.
International Search Report and Written Opinion for PCT/US2014/072518 dated Jul. 23, 2015 in 15 pages.
Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).
Davison, J.A., Chapter 11: Intraocular Lenses, *Duane's Clinical Ophthalmology on CD-ROM*, Lippincott Willliams & Wilkins, 2005, vol. 6, pp. 1-46.

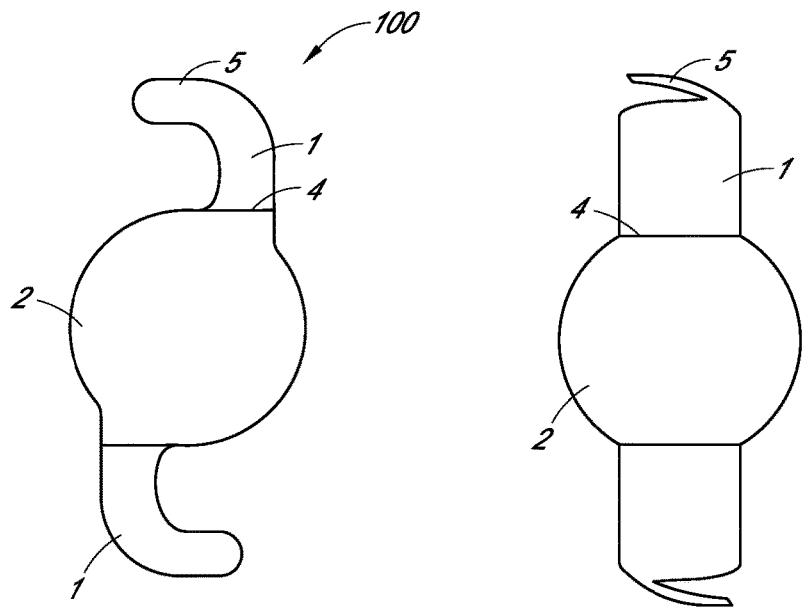
FIG. 1
FIG. 2
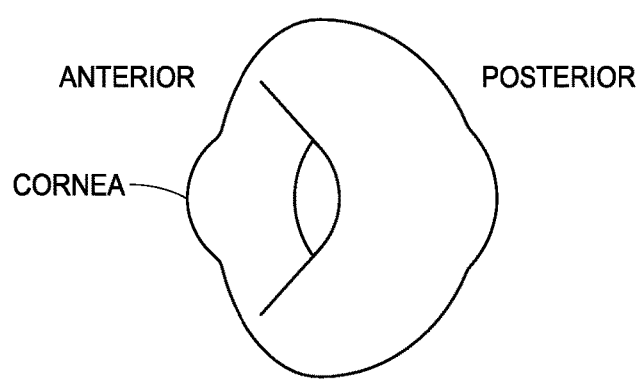
FIG. 4
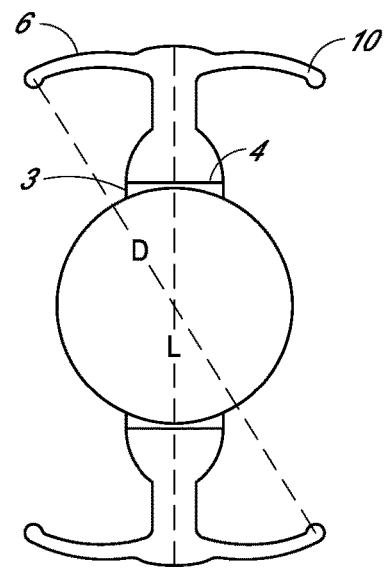
FIG. 3

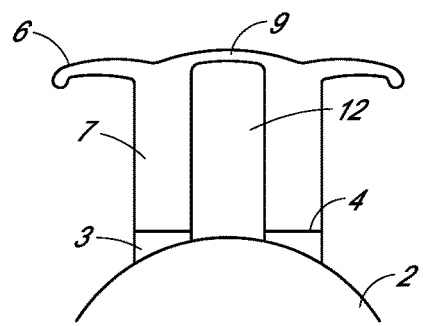
FIG. 5
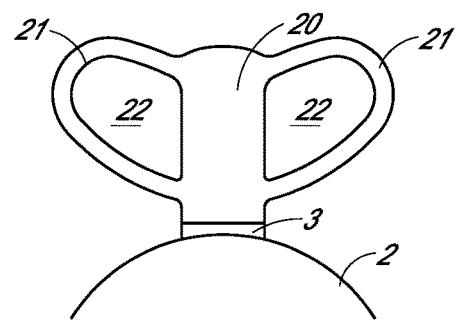
FIG. 6
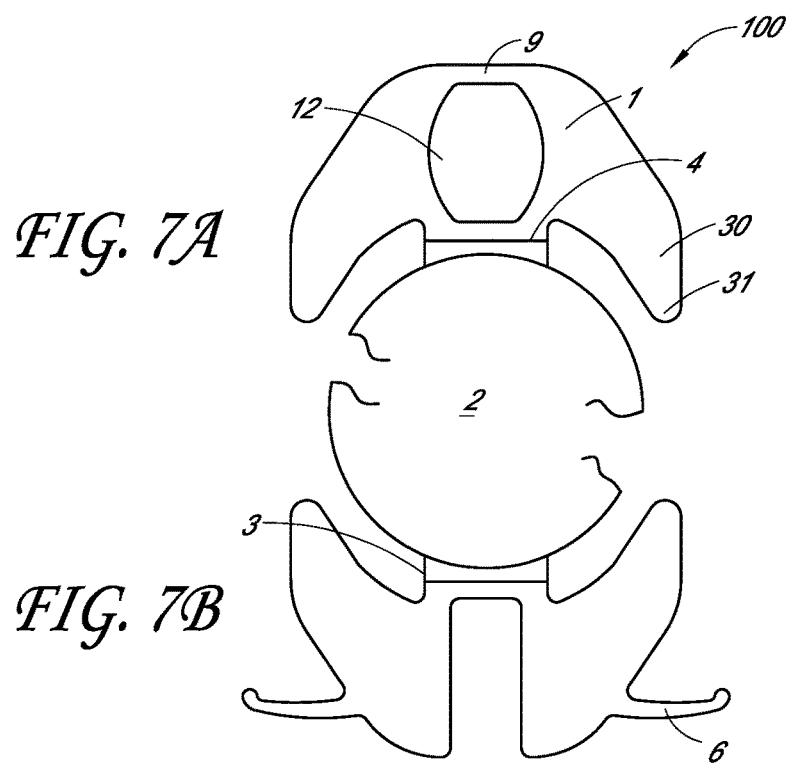
FIG. 7A
FIG. 7B

US 9,655,717 B2

SEMI-FLEXIBLE POSTERIORLY VAULTED ACRYLIC INTRAOCULAR LENS FOR THE TREATMENT OF PRESBYOPIA

CROSS-REFERENCE TO RELATED APPLICATIONS

This application is a continuation of U.S. patent application Ser. No. 14/257,933, filed on Apr. 21, 2014, currently pending, which is a continuation-in-part of U.S. patent application Ser. No. 14/143,612, filed on Dec. 30, 2013, currently pending, the contents of which are hereby incorporated by reference herein in their entireties.

BACKGROUND

The present disclosure relates to non-accommodating single focus intraocular lenses to provide uncorrected vision at all distances. The lens having haptics and an optic comprising a semi-rigid acrylic that can be deformed for implantation into the eye through a small incision, but can regain its optical and physical properties after implantation into the eye and resist deformation when force is applied by the ciliary muscle and by fibrosis.

DESCRIPTION OF THE RELATED ART

Surgical procedures for treating cataracts that are commonly employed today involve implanting an intraocular lens (IOL) into the eye. In such procedures, a normal human lens that has been clouded over by a cataract is typically replaced by the IOL that is inserted into the capsular bag of the human crystalline lens following cataract surgery.

Many breakthrough changes in cataract surgery during the last forty years have yielded a reliable surgical procedure that regularly produces favorable patient outcomes. Modern surgical techniques also have made removing the human lens and replacing it with an artificial lens very safe when performed by a competent surgeon.

The procedure can now also be considered a surgical means of treating myopia, hyperopia, astigmatism and presbyopia as IOLs with the appropriate power to provide optical correction can be inserted in the eye.

SUMMARY OF THE INVENTION

Recently lenses have been developed to treat presbyopia. There are two types: multifocal and accommodating. Since the light entering the eye has more than one focal point, patients implanted with multifocal lenses have problems with halos, glare, foggy vision and reduced contrast sensitivity, since less than half of the light is in focus at one time. Many of these lenses have had to be explanted because of these problems. Accommodating lenses have also been invented which were designed to move forward upon constriction of the ciliary muscle with near vision. The near vision with these lenses is not as good as that with the multifocal lenses, however they do not have the problems that are associated with multifocal lenses.

Two of the remaining problems to be solved are to make the post-operative uncorrected distance visions more accurate than they are now, and to provide excellent uncorrected distance, near and intermediate vision with a single focus lens. This would then make lens surgery comparable to corneal surgery so far as the uncorrected visions are concerned, making common surgical cataract surgery or removal of a clear lens, a refractive procedure safer and with less complications than corneal refractive and corneal presbyopic surgery.

Certain aspects of the disclosure are directed toward an intraocular lens having a single-focus, acrylic optic and at least one semi-rigid, acrylic haptic connected to the optic. The intraocular lens can have a fixed longitudinal length (e.g., the same fixed length pre-operatively and post-operatively). The intraocular lens can resist deformation, despite contraction and relaxation of the ciliary muscle and fibrosis within the capsular bag, after implantation into the eye using, for example, the semi-rigid haptics described herein. The intraocular lens can be sufficiently flexible to be compressed from an original configuration to a compressed configuration for insertion into the eye through a small incision and return to a normal shape (e.g., uncompressed shape) after implantation into the eye. The intraocular lens can be configured to provide uncorrected visional at near, intermediate, and far distances.

In the above-mentioned intraocular lens aspect, the optic can be vaulted backwards at a fixed angle relative to the at least one haptic. The vault angle can remain unchanged after implantation into the eye. In certain aspects, the at least one haptic can be biased anteriorly. In certain aspects, the at least one haptic can include two haptics that are both biased anteriorly. In certain aspects, the vault angle can be between about 1 degree and about 50 degrees.

In some embodiments, the semi-rigid haptic can include at least one longitudinally extending strut. In certain aspects, the rigid structure can include a closed structure at least partially surrounding the at least one longitudinally extending strut to form at least one open area (e.g., one, two, or three open areas). In certain aspects, the loop structure can include a first width and a second width. The first width can be closer to a distal end of the loop structure, and the first width can be greater than the second width. In certain aspects, the loop structure can have a width that is less than the width of the at least one longitudinally extending strut. For example, the width of the loop structure can be less than about 25% and/or greater than about 5% of the width of the at least one longitudinally extending strut (e.g., less than 20%, less than 15%, or less than 10%).

In some embodiments, the semi-rigid haptics may have compressible thin T-shaped lateral flexible fingers at the distal end of the otherwise semi-rigid haptic.

In some embodiments, the semi-rigid structure can be a plate haptic. The plate haptic can include flexible thin distal lateral T-shaped fingers.

In some embodiments, the semi-rigid haptic may be more rigid than the flexible optic. The optic can be flexible at its thin circumference and semi-rigid at its center, thus allowing it to be folded into a longitudinally elongate configuration to be inserted through a small incision into the eye having a length of less than or equal to about 3.0 mm, preferably less than or equal to about 2.5 mm. The intraocular lens can be a non-accommodating IOL designed to provide excellent distance, intermediate and near vision without the problems of glare, halos and foggy vision and reduced contrast experienced with multifocal intra ocular lenses.

In some embodiments, the posterior vaulted optic connects to a haptic of the same semi-rigid material, the haptic made more rigid by widening or thickening its structure or by a combination of both.

Certain aspects of the disclosure are directed toward a non-accommodating intraocular lens having a single-focus optic and at least one semi-rigid haptic connected to the optic. The optic can be pre-operatively vaulted (e.g., posteriorly) at a fixed angle relative to the at least one haptic. The vault angle can remain unchanged after implantation. The semi-rigid haptic can be sufficiently flexible to be compressed for insertion into the eye through a small incision and assume a normal, uncompressed shape after implantation into the eye. The lens can be configured to provide uncorrected vision at near, intermediate, and far distances.

In the above-mentioned non-accommodating intraocular lens, the at least one semi-rigid haptic can be biased anteriorly. In certain aspects, the at least one semi-rigid haptic includes two haptics that are both biased anteriorly.

In any of the above-mentioned non-accommodating intraocular lenses, the vault angle can be between about 1 degree and about 50 degrees, such as between about 5 degrees and about 40 degrees.

In any of the above-mentioned non-accommodating intraocular lenses, the optic and the at least one haptic can include a same material (e.g., acrylic or silicone). Certain aspects of the disclosure are directed toward implanting a non-accommodating intraocular lens having an optic connected to at least one haptic. The intraocular lens can have any of the features described herein. Pre-operatively the intraocular lens can be vaulted at posteriorly at a fixed angle relative to the at least one haptic. The intraocular lens can be compressed for insertion into the eye through a small incision. After implantation, the intraocular lens can assume a normal, uncompressed shape that is resistant enough to withstand the pressure changes within the eye, e.g., caused by the ciliary muscle attempting to accommodate or by fibrosis. After implantation, the intraocular lens can remain vaulted at the same fixed angle.

Certain aspects of the disclosure are directed toward a non-accommodating intraocular lens having a single-focus, acrylic optic and at least one haptic connected to the optic. The optic can be pre-operatively vaulted at a fixed angle relative to the at least one haptic. The vault angle can remain unchanged after implantation. The intraocular lens can be configured to provide uncorrected visional at near, intermediate, and far distances.

In the above-mentioned non-accommodating intraocular lens, the at least one haptic can be biased anteriorly. In certain aspects, the at least one haptic can include two anteriorly biased haptics.

In any of the above-mentioned non-accommodating intraocular lens, the vault angle can be between about 1 degree and 50 degrees, such as between about 5 degrees and about 40 degrees.

In any of the above-mentioned non-accommodating intraocular lens, the optic and the at least one haptic can include a same material.

A wide variety of variations is possible. For example, any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein.

BRIEF DESCRIPTION OF THE FIGURES

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1 illustrates a non-accommodating lens with wide flat loops (e.g. open loops) that comprises a posteriorly vaulted optic and haptics manufactured in one piece (e.g., monolithic) from acrylic.

FIG. 2 illustrates a plate haptic non-accommodating intraocular lens with a posteriorly vaulted optic with small thin flexible fixation loops manufactured as one monolithic piece.

FIG. 3 illustrates an embodiment of a haptic having a single thick rigid longitudinal anteriorly vaulted haptic structure with T-shaped flexible distal lateral extensions.

FIG. 4 is a schematic representation of the posterior vaulting in certain lens designs in this application.

FIG. 5 illustrates another lens design having two thick rigid longitudinal plates or struts 7 connected by a thin, transverse bar 9 creating an enclosed open space 12 (e.g. closed loops) to facilitate fixation of the lens into the capsular bag along with distal lateral thin flexible fingers 6. The lens may be designed without the flexible fingers since fixation can occur over the transverse thin bar 9. The thin arm 9 can have a width that is less than a width of the longitudinal plate or struts 7.

FIG. 6 is a lens design with a thick central longitudinal plate 20 having a width of less than about 3.0 mm and two closed loops 21 providing two open spaces 22 for fixation of the lens into the capsular bag.

FIG. 7A illustrates one-half of a lens with a haptic 1 having lateral members 30. The haptic 1 can be wider than the optic 2, and the tip 31 of the lateral members 30 can be designed to lie posterior to the optic. The haptic 1 forms a closed loop 12.

FIG. 7B illustrates one-half a lens with a haptic 1 having lateral members 30. The haptic 1 can be wider than the optic with finger-like flexible lateral extensions 6.

DETAILED DESCRIPTION OF THE PREFERRED EMBODIMENTS

Many intraocular lenses have an optic connected to two or more flexible haptics, which function to center and fixate the lens in the empty capsular bag of the human lens. These haptics include open flexible loops or closed loops and plate haptics.

The circular ciliary muscle inside the eye, part of the autonomic nervous system and active throughout life, is responsible for changing the focus of the eye in people up to the age of forty. When a patient implanted with standard flexible loop haptic intraocular lenses, attempts to see during the early post-operative period following cataract surgery the ciliary muscle, still active, tightens and relaxes the zonules that connect the muscle to the capsular bag into which the lens has been placed at the time of surgery. Contraction and relaxation of the ciliary muscle causes a simultaneous increase and decrease in the pressure in the posterior and anterior chambers of the eye. This movement and the pressure changes can shift the location of the lens in the capsular bag during the early post-operative period. This along with fibrosis can exert forces onto the lens design such that the loops do not necessarily end up fixed in the cul-de-sac of the bag where they were placed at the time of surgery. Instead, the loops may be, for example, stuck somewhere between the cul-de-sac of the capsular bag and the optic, and the optic may be decentered and/or be tilted.

Changing the location of the haptic loops within the bag can also change the effective lens position (ELP) of the lens optic along the axis of the eye and cause de-centration and tilting of the optic, and adversely affect the expected post-operative refraction. In many of these flexible loop designs, these flimsy flexible loops at the time of manufacture are significantly longer than the 10 mm diameter of the capsular bag (e.g., up to 12 mm long) and may impinge through the capsular bag wall to impinge on the ciliary muscle. The haptics are flimsy and are easily deformed by the pressures exerted on them during the early post-operative period. The lens position is thus not where it was calculated and anticipated to be. Consequently, the uncorrected distance vision (e.g. without glasses or contact lenses) and post-operative refractions are not what was expected prior to surgery. In some cases, the thin flexible loops of a lens have been compressed centrally to lie in front or behind, the lens optic.

Various embodiments described here comprise intraocular lens structures that more accurately place the optic of an intraocular lens in a more consistently repeatable and predictable location along the optical or visual axis of the eye in comparison to other lens designs, thereby making post-operative uncorrectable vision (e.g., without the aid of eyeglasses or contacts) more predictable.

This disclosure, for example, describes an intraocular lens comprising at least one semi-rigid haptic (e.g., two, three, or more) and an optic. In some embodiments, the at least one semi-rigid haptic and the optic can comprise a same material (e.g., acrylic). In some embodiments, the intraocular lens can be monolithic or a single piece. The semi-rigid haptics and optic may be foldable, in order to insert the optic through a small incision into the eye. However, after insertion and regaining its shape it is resistant enough to withstand the pressure changes within the eye that occur with contraction and relaxation of the ciliary muscle and from the forces that occur during postoperative fibrosis. The two semi-rigid haptics can have equal length. Resistance to deformation by the action of the ciliary muscle and fibrosis leave the lens optic in substantially the same position along the optical or visual axis of the eye as it was when it was placed into the empty capsular bag at the time of surgery. The lens may be designed to be slightly longer, or shorter, than the capsular bag and may be angulated, having a fixed angle at the time of manufacture, of between about 1 degree and 50 degrees, such as between about 5 degrees and about 40 degrees (e.g., between about 5 degrees and about 20 degrees, between about 10 degrees and about 25 degrees, between about 15 and about 40 degrees), to, for example, achieve optimal depth of focus. This will position the lens optic in a posterior position relative to the distal ends of the haptics upon insertion into the capsular bag (see FIG. 4).

Various embodiments are directed toward a non-accommodating intraocular lens with the optic manufactured in one piece with the optic vaulted backwards, wherein the vault angle may be the same on both optic/haptics junctions. The semi-rigid lens structure can be resistant to deformation by the ciliary muscle and fibrosis, but can be foldable longitudinally to be inserted through an incision of less than 4.0 mm into the capsular bag of the eye. Additional details related to structures that permit such functionality can be found in U.S. application Ser. No. 14/143,612, titled "FOLDABLE INTRAOCULAR LENS WITH RIGID HAPTICS," filed Dec. 30, 2013, which is incorporated hereby by reference in its entirety and which makes it plain that the lens of the present invention can be uniplanar, have a fixed length and be capable of vaulting posteriorly after insertion in the eye to provide consistent and predictable location of the optic in a position posterior to the haptic. This will provide seamless, uncorrected vision for distance, intermediate and near vision.

The overall longitudinal length of the lens can be between about 9.5 and about 12 mm, which may be slightly longer than the capsular bag, preferably about 10.5 mm. Both semi-rigid haptics can be the same length. The diameter of the optic can be between 4.0 and 8 mm with a thin center thickness between about 0.2 and about 2.0 mm. Since the semi-rigid material is resistant to deformation by the ciliary muscle and fibrosis, the haptics cannot be significantly deformed and, therefore, the lens optic is in the same position post operatively as it was at the time of surgery. Similarly, orientation of the intraocular lens can be the same post-operatively as pre-operatively both along the axis of the eye and on a rotational axis should a toric lens be implanted. This makes the predictability of the post-operative effective lens position (ELP) along the visual axis of the eye more accurate and, therefore, the uncorrected visions are more predictable. The longitudinal length of the intraocular lens can be fixed prior to insertion into the eye, e.g., the longitudinal length of the intraocular lens can be the same pre-operatively and post-operatively. However, the lens may have thin flexible distal lateral fingers resulting in the transverse diameter being longer than the longitudinal diameter. These flexible fingers can be designed to fixate the lens within the capsular bag and prevent rotation of the lens when a toric optic is part of the lens design.

The longitudinally rigid haptic can comprise the same material as the flexible optic and be manufactured as one piece. The semi-rigid haptic can be made more rigid by increasing its thickness and/or its width. Fixation can be done using flexible loops (open or closed loops) contiguous with the lens body extending tangentially from the distal lateral aspects of the plate haptic design, or by creating open spaces within the confines of the diameter of the haptic, or by closed loops extending beyond the diameter of the optic. The loops of the semi-rigid material may be thin to be flexible and compressible, but rigid enough to maintain the length of the lens when subject to forces from the ciliary muscle.

Various embodiments disclosed herein, however, can address the problems discussed above. See, for example, the intraocular implants illustrated in FIGS. 1-3. The intraocular implants comprise an optic 2 and opposing anteriorly biased semi-rigid haptics 1, directly connected to the optic, at the flexible junction 4, with flexible loop lateral extensions 5 (e.g. open loops). In FIGS. 5 and 6, only one of the two halves of the lens is shown. The lens can have two-fold symmetry, such that the other half is the same as that shown. A short optic extension 3 can include the flexible junction 4 between the optic 2 and the haptic 1. The optic 2 and haptics 1 can be constructed from the same material (e.g., acrylic). The short optic extension 3 may be desirable to facilitate the connection between the optic 2 and the haptic 1 without the haptic 1 encroaching on the circumference of the optic 2.

The lens 100 may comprise a transparent biocompatible flexible optical material, such as acrylic, and the optic may be biconvex, plano convex, concave/plano, toric, aspheric, spherical, Fresnel, multifocal or any combination, thereof.

The haptics 1, in at least the longitudinal direction, are designed to be semi-rigid and resistant to deformation from the action of the ciliary muscle or by fibrosis. Unlike flexible haptics that are traditionally used with non-accommodating and accommodating lenses, the semi-rigid longitudinal haptics 1 better facilitate centration and provide a more consistent location of the optic along the axis of the eye because the longitudinally semi-rigid haptics 1 are resistant to deformation.

FIG. 4 schematically demonstrates the fixed posterior vaulting of all the lenses, in embodiments of the intraocular lenses described herein. The overall length of the lens 100 may be from about 9.5 mm to about 12.0 mm, and from about 11.0 mm to about 14.0 mm as measured diagonally across the lens from the tips 10 of the fixation flexible lateral loops 6 on opposite sides of the lens. See, e.g., FIG. 3. The lateral loops 6 can include orientation members 10 (e.g., round or oval knobs, one on each end of the fixation members) at an end of the lateral loops 6. The diagonal distance extends through the center of the optic. The longitudinal length L of the lens 100 (also shown in FIG. 3) can be at least the diameter of the average capsular bag. For example, the preferred longitudinal length can be about 10.5 mm.

The short optic extension 3 extending from the flexible optic can be made more rigid in some embodiments by its shorter length of less than 1 mm, and its thickness.

As shown in FIG. 7A, the haptics 1 can have lateral members 30 and a transverse bar 9 extending between the lateral extension members 30. The haptic 1 can be wider than the optic 2, and the tip 31 of the lateral members 30 can be designed to lie posterior to the optic. The lateral members 30 can thus be increasingly curved toward the tip 31. The haptic 1 can form a closed loop 12. The intraocular lens can include a short optic extension 3 across which is the rigidly flexed junction 4 between the optic 2 and the haptic 1.

As shown in FIG. 7B, the haptics 1 can have lateral members 30 having distal arcuate outer edges becoming parallel to the longitudinal length proximally to the optic. The haptic 1 can be wider than the optic with finger like flexible lateral extensions 6. The lateral members 30 can be connected by a short optic extension 3 across which is the rigidly flexed junction 4 between the optic 2 and the haptic 1. In some embodiments, the haptics 1 partially surround the optic by more than 180° of the circumference of the optic.

As used herein, the relative terms "proximal" and "distal" shall be defined from the perspective of the optic. Thus, proximal refers to the direction toward the optic, and distal refers to the direction away from the optic.

As used herein, the terms "fixed length" or "fixed longitudinal length" refer to a change in length that is less than or equal to about 5% (e.g., less than or equal to about 4%, less than or equal to about 3%, less than or equal to about 2%, or less than or equal to about 1%) after implantation when subject to a force exerted by the ciliary muscle. For example, flexible fingers 5 may flex centrally to fixate the intraocular lens in the capsular bag (see FIG. 2). As used herein, the phrase "vault angle can remain unchanged" refers to a change that is less than or equal to about 5% (e.g., less than or equal to about 4%, less than or equal to about 3%, less than or equal to about 2%, or less than or equal to about 1%) after implantation when subject to a forces from the ciliary muscle and by fibrosis.

Conditional language, such as "can," "could," "might," or "may," unless specifically stated otherwise, or otherwise understood within the context as used, is generally intended to convey that certain embodiments include, while other embodiments do not include, certain features, elements, and/or steps.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 5% of the stated amount.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Although certain embodiments and examples have been described herein, it will be understood by those skilled in the art that many aspects of the intraocular lenses shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:
1. A monolithic uniplanar intraocular lens comprising:
    a semi rigid optic capable of being vaulted posteriorly;
    a pair of plate haptics which are sufficiently longitudinally rigid to resist deformation by the ciliary muscle of the eye or by fibrosis coupled to opposite sides of the optic by a flexible junction;

said haptics being configured with rigid lateral members extending from said plates and partially surrounding said optic; and said intraocular lens being foldable about its longitudinal axis such that it can be inserted into the eye through a small incision and being capable of returning to its original configuration after insertion.

2. The intraocular lens of claim 1, wherein said haptics are provided with flexible lateral fingers at their distal regions.

3. The intraocular lens of claim 2, wherein said fingers have knobs at their distal ends.

4. The intraocular lens of claim 1, wherein said haptics are provided with loops configured to engage the capsular bag of an eye.

5. The intraocular lens of claim 4, wherein said loops are closed loops.

6. The intraocular lens of claim 4, wherein said loops are open loops.

7. The intraocular lens of claim 1, wherein the optic and haptic comprise the same material.

8. The intraocular lens of claim 7, wherein the same material is acrylic.

9. The intraocular lens of claim 1, wherein said lens is non-accommodating.

10. The intraocular lens of claim 1, wherein said lens has a fixed length.

11. The intraocular lens of claim 1, wherein said optic is provided with an extension which extends distally from said optic to the proximal end of each haptic and has a flexible junction with the haptic.

12. The intraocular lens of claim 1, wherein said flexible junction is capable of being flexed after implantation in the eye to vault the optic posteriorly.

13. A uniplanar intraocular lens comprising:

a single-focus, semi-rigid acrylic optic, the optic being vaulted backwards; and a pair of semi-rigid, acrylic haptics connected to opposite sides of the optic, each haptic comprising a plate haptic, wherein the intraocular lens has a fixed longitudinal length, the fixed longitudinal length being measured from the distal end of one of the haptics to the distal end of the other of the haptics and along a longitudinal axis of the intraocular lens, the fixed longitudinal length being the same pre-operatively and post-operatively, such that the intraocular lens haptics resist deformation during contraction and relaxation of the ciliary muscle and fibrosis to maintain the optic in the same position along an optical axis of the eye, the fixed longitudinal length being between 9.5 mm and about 12 mm, the lens configured to provide uncorrected vision at near, intermediate and far distances without accommodation.

14. The intraocular lens of claim 13, wherein the optic is vaulted backwards at a fixed angle relative to each haptic, the vault angle remaining unchanged after implantation into the eye.

15. The intraocular lens of claim 14, wherein the vault angle can be between about 1 degree and about 50 degrees.

16. The intraocular lens of claim 15, wherein the vault angle can be between about 5 degrees and about 40 degrees.

17. The intraocular lens of claim 13, wherein the at least one semi-rigid haptic further comprises an enclosed, open area formed at least partially by a thin bar.

18. The intraocular lens of claim 13, wherein each haptic further comprises at least one lateral extension extending from a distal end of the haptic.

19. The intraocular lens of claim 13, wherein each haptic comprises a flat, curved open loop haptic.

20. The intraocular lens of claim 13, wherein each haptic comprises a single, longitudinal plate with at least one flexible finger loop extending laterally from a proximal end of the plate to a distal end of the plate to form at least one open area.

21. The intraocular lens of claim 20, wherein the at least one open area comprises two or three open areas.

22. The intraocular lens of claim 13, wherein each semi-rigid haptic is connected to the optic by a semi-rigid extension of the optic.

23. A non-accommodating intraocular lens comprising:

a single-focus optic; and a pair of semi-rigid haptics connected to opposite sides of the optic, wherein the optic is pre-operatively vaulted posteriorly at a fixed angle relative to each haptic, the vault angle remaining unchanged after implantation, the vault angle being between 1 degree and 50 degrees, the lens configured to provide uncorrected vision at near, intermediate and far distances without accommodation, wherein the semi-rigid haptic is sufficiently flexible to be compressed from an original configuration to a compressed configuration for insertion into the eye through a small incision and sufficiently rigid to resist compression when subject to pressures by the ciliary muscles and fibrosis, the intraocular lens being configured to return to the original configuration after implantation, the original configuration being vaulted posteriorly at the fixed angle, and wherein an outmost lateral periphery of the haptics has a transverse dimension larger than that of the optic and surrounding at least a portion of the periphery of the optic and a lateral side of each haptic.

24. The non-accommodating intraocular lens of claim 23, wherein the optic and the at least one haptic comprise a same material.

25. The non-accommodating intraocular lens of claim 24, wherein the same material is acrylic.

26. A non-accommodating intraocular lens comprising:

a single-focus, acrylic optic; and a pair of acrylic haptics connected to opposite sides of the optic, each haptic having a proximal end and a distal end, the proximal end being closer to the optic than the distal end, wherein the lens optic is manufactured vaulted posteriorly at a fixed angle relative to each haptic, the vault angle remaining unchanged after implantation, the vault angle being between 1 degree and 50 degrees, the lens configured to provide uncorrected vision at a near, intermediate and far distances without accommodation, wherein the intraocular lens has a fixed longitudinal length, the fixed longitudinal length being measured from the distal end of one of the haptics to the distal end of the other of the haptics and along the longitudinal axis of the intraocular lens, the fixed longitudinal length being the same pre-operatively and post-operatively, such that the intraocular lens resists deformation during contraction and relaxation of the ciliary muscle and fibrosis to maintain the optic in the same position along an optical axis of the eye, the fixed longitudinal length between about 9.5 mm and 12 mm, and wherein the optic and the at least one haptic are monolithic.

27. The non-accommodating intraocular lens of claim 26, wherein the vault angle can be between about 5 degrees and about 50 degrees.

28. The non-accommodating intraocular lens of claim 26, wherein the optic and the pair of haptics comprise the same material.

* * * * *